United States Patent [19]

Roantree et al.

[11] 4,407,808
[45] Oct. 4, 1983

[54] 2-HETEROCYCLIC ALKYLAMINO-3-NITROPYRROLES

[75] Inventors: Michael L. Roantree, Welwyn Garden City; Rodney C. Young, Bengeo, both of England

[73] Assignee: Smith Kline & French Laboratories Limited, Welwyn Garden City, United Kingdom

[21] Appl. No.: 343,632

[22] Filed: Jan. 28, 1982

Related U.S. Application Data

[62] Division of Ser. No. 159,524, Jun. 16, 1980, Pat. No. 4,331,668, which is a division of Ser. No. 43,786, May 30, 1979, Pat. No. 4,238,494.

[30] Foreign Application Priority Data

May 30, 1978 [GB] United Kingdom ............... 24117/78
Aug. 4, 1978 [GB] United Kingdom ............... 32313/78

[51] Int. Cl.$^3$ .................... A61K 31/40; C07D 403/12; C07D 413/12; A61K 31/41

[52] U.S. Cl. .................................. 424/263; 424/269; 424/272; 546/276; 546/281; 548/225; 548/226; 548/233; 548/235; 548/243; 548/245; 548/247; 548/264; 548/265; 548/266; 548/269

[58] Field of Search ............... 548/225, 226, 233, 235, 548/243, 245, 247, 264, 265, 266, 269; 546/276, 281; 424/263, 269, 272

[56] References Cited

U.S. PATENT DOCUMENTS

| | | | |
|---|---|---|---|
| 3,518,251 | 6/1970 | Gatzi ................................... | 546/264 |
| 3,932,644 | 1/1976 | Durant et al. ....................... | 424/263 |
| 3,953,460 | 4/1976 | Durant et al. ................... | 424/273 R |
| 4,128,658 | 12/1978 | Price et al. ......................... | 546/201 |
| 4,154,834 | 5/1979 | Brown et al. ....................... | 548/343 |

Primary Examiner—Henry R. Jiles
Assistant Examiner—Natalia Harkaway
Attorney, Agent, or Firm—Joan S. Keps; Richard D. Foggio; Alan D. Lourie

[57] ABSTRACT

3-Nitro-2-substituted aminopyrroles are histamine $H_2$-receptor antagonists. The 2- position substituent is a fully-unsaturated heterocyclyl alkyl group preferably with alkyl group interrupted by sulfur or oxygen. The 4- and 5- positions of the pyrrole ring can also be substituted.

5 Claims, No Drawings

2-HETEROCYCLIC ALKYLAMINO-3-NITROPYRROLES

This is a division of application Ser. No. 159,524 filed June 16, 1980, now U.S. Pat. No. 4,331,668, which is a division of application Ser. No. 043,786, filed May 30, 1979, now U.S. Pat. No. 4,238,494.

This invention relates to nitro compounds having activity as histamine $H_2$-receptor antagonists, pharmaceutical compositions containing them and methods of inhibiting histamine $H_2$-receptors by administering these compounds.

Many physiologically active substances elicit their biological actions by interaction with specific sites known as receptors. Histamine is such a substance and it has multiple biological actions. Those biological actions of histamine which are inhibited by drugs commonly called "antihistamines", of which mepyramine, diphenhydramine and chloropheniramine are typical examples, are mediated through histamine $H_1$-receptors. However, others of the biological actions of histamine are not inhibited by "antihistamines", and actions of this type which are inhibited by burimamide are mediated through receptors which are termed histamine $H_2$-receptors, and $H_2$-receptors are defined as those histamine receptors which are not blocked by mepyramine but are blocked by burimamide. Compounds which block histamine $H_2$-receptors are referred to as histamine $H_2$-receptor antagonists.

Blockade of histamine $H_2$-receptors is of value in inhibiting the biological actions of histamine which are not inhibited by "antihistamines". Histamine $H_2$-receptor antagonists are therefore useful, for example, as inhibitors of gastric acid secretion, as anti-inflammatory agents, and as agents which act on the cardiovascular system, for example as inhibitors of the effects of histamine on blood pressure.

The compounds of this invention are represented by Structure 1:

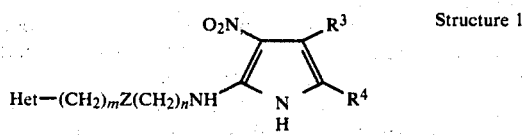

Structure 1 in which

Het is a 5- or 6- membered, fully-unsaturated heterocycle containing at least one nitrogen atom and being optionally substituted by lower alkyl, trifluoromethyl, hydroxymethyl, halogen, hydroxy, lower alkoxy or amino, or a fully-unsaturated 5-membered heterocycle containing one oxygen or sulfur atom as the sole heteroatom i.e. furyl or thienyl and substituted by a group $R^1R^2N$—A— where $R^1$ and $R^2$, which can be the same or different, are each hydrogen, lower alkyl, $C_3$–$C_6$ cycloalkyl, lower alkenyl, aryl lower alkyl, lower alkyl substituted by lower alkoxy, (lower alkyl)amino or di(lower alkyl)amino, or $R^1$ and $R^2$ together with the nitrogen atom to which they are attached form a pyrrolidino or piperidino ring, and A is a straight or branched $C_1$–$C_6$ alkanediyl group;

Z is sulphur, methylene or oxygen;

m is 0, 1 or 2 and n is 2 or 3 provided that m+n is 3 or 4;

$R^3$ is hydrogen, lower alkyl, aryl, aryl lower alkyl or heteroaryl lower alkyl; and $R^4$ is hydrogen or lower alkyl.

The compounds of Structure 1 can be in the form of the free bases or pharmaceutically acceptable acid addition salts thereof.

Herein, 'lower alkyl', and 'lower alkoxy' are respectively used to mean alkyl and alkoxy groups having 1 to 4 carbon atoms which can be straight or branched, and 'lower alkenyl' is used to mean alkenyl groups containing from 3 to 6 carbon atoms which can be straight or branched.

Examples of nitrogen-containing heterocycles for Het are imidazole, pyridine, thiazole, isothiazole, oxazole, isoxazole, 1,2,4-triazole, 1,2,5-thiadiazole and 1,3,4-thiadiazole. The group $(CH_2)_m$ is preferably linked to a carbon atom of the heterocycle Het adjacent to a nitrogen atom. The heterocycle of Het is preferably imidazole. In particular, Het can be 2- or 4- imidazolyl optionally substituted by lower alkyl (especially methyl), halogen (especially chlorine or bromine), trifluoromethyl or hydroxymethyl. Other suitable groups Het are 2-pyridyl optionally substituted by lower alkyl (especially methyl), lower alkoxy (especially methoxy), halogen (especially chlorine or bromine), amino or hydroxy; 2-thiazolyl; 3-isothiazolyl optionally substituted by chlorine or bromine; 3-(1,2,5)-thiadiazolyl optionally substituted by chlorine or bromine and 2-(5-amino-1,3,4-thiadiazolyl). Specific examples of groups Het are 5-methyl-4-imidazolyl, 5-bromo-4-imidazolyl, 3-bromo-2-pyridyl, 3-chloro-2-pyridyl, 3-methoxy-2-pyridyl and 3-hydroxy-2-pyridyl.

When Het is a 5- membered heterocycle containing one oxygen as the sole heteroatom furyl, the group $(CH_2)_m$ is preferably linked to a carbon atom of the heterocycle adjacent to the hetero atom. The group $R^1R^2N$—A— is preferably linked to the other carbon atom of the heterocyclic adjacent to the oxygen atom. $R^1$ and $R^2$ are preferably hydrogen, lower alkyl (especially methyl), phenyl(lower alkyl) where the phenyl group is optionally substituted by lower alkyl, lower alkoxy or halogen, or di(lower alkyl)amino(lower alkyl). A is preferably an α,ω-straight alkylene group containing from 1 to 3 carbon atoms, particularly methylene. Specific examples of such groups Het are 5-(4-dimethylamino)butyl)-2-furyl and 5-(dimethylamino)-methyl)-2-furyl.

Preferably Z is sulphur.

Preferably m is 1 and n is 2.

$R^3$ is preferably hydrogen, methyl, aryl, arylmethylene or heteroarylmethylene. Examples of aryl groups and the aryl moiety of arylmethylene groups for $R^3$ are phenyl optionally substituted with one or more lower alkyl, lower alkoxy or halogen groups, particularly 3-methylphenyl, 3-methoxyphenyl, 3,4-dimethoxyphenyl and 3-chlorophenyl, 5- or 6-(2,3-dihydro-1,4-benzodioxinyl) and 4- or 5-(1,3-benzodioxolyl). Examples of heteroaryl groups for $R^3$ are 2-furyl, 2-thienyl, 2-pyridyl, 3-pyridyl or 4-pyridyl, which groups are optionally substituted by one or more lower alkyl or lower alkoxy groups, and particularly 3-pyridyl, 6-methyl-3-pyridyl and 6-methoxy-3-pyridyl.

$R^4$ is preferably methyl, and more preferably $R^4$ is hydrogen.

Examples of specific compounds of the invention are:
2-[2-(5-methyl-4-imidazolylmethylthio)ethylamino]-3-nitropyrrole 2-[2-(5-methyl-4-imidazolylmethylthio)ethylamino]-3-nitro-4-methylpyrrole 2-[2-(5-methyl-4-imidazolylmethylthio)ethylamino]-3-nitro-4-benzylpyrrole 2-[2-(5-methyl-4-imidazolylmethylthio)ethylamino]-3-nitro-4-(2-phenylethyl)pyrrole 2-[2-(methyl-4-imidazolylmethylthio)ethylamino]-3-nitro-4-phenylpyrrole 2-[2-(5-methyl-4-imidazolylmethylthio)ethylamino]-3-nitro-4-n-butylpyrrole 2-[(3-chloropyrid-2-yl)methylthio]ethylamino-3-nitropyrrole and 2-(5-dimethylaminomethyl-2-furylmethylthio)ethylamine.

The compounds of Structure 1 can be prepared by reacting a compound of formula Het-$(CH_2)_mY$ where Y is $-Z(CH_2)_nNH_2$ or optionally when m is 1 or 2 a leaving group displaceable by a mercaptan, for example halogen, trisubstituted phosphonium (for example triphenylphosphonium) or substituted sulphonyloxy (for example p-toluenesulphonyloxy, methanesulphonyloxy or trifluoromethanesulphonyloxy) with a compound of Structure 2:

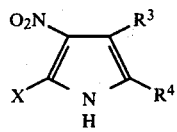

Structure 2 where X is QSO— or $QSO_2$—(where Q is lower alkyl, aryl or arylalkyl, or another leaving group which is displaceable with an amine) when Y is $-Z(CH_2)_nNH_2$, and X is $HS(CH_2)_nNH$— when Y is a leaving group displaceable by a mercaptan. This reaction is preferably carried out in the presence of a solvent, for example a lower alkanol. In general, an elevated temperature will be used, for example the boiling point of the reaction mixture. X is preferably QSO— Q preferably being methyl or benzyl. It will be appreciated that when $R^1$ and $R^2$ are hydrogen or are lower alkyl substituted by (lower alkyl)amino it may be necessary to protect amino groups in the $R^1R^2N$—A— substituents of compounds of the formula Het$(CH_2)_mY$ to prevent competing side reactions.

The compounds of Structure 1 and the intermediate compounds of Structure 2 where X is QSO— or $QSO_2$— can be prepared by reaction of a compound of Structure 3

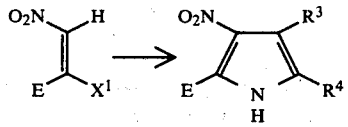

Structure 3      Structure 4 in which E is Het—$(CH_2)_mZ(CH_2)_nNH$— or QS— and $X^1$ is QS— or (when E is QS—) QSO— with an aminoketone of formula $H_2NCHR^4COR^3$ or an aminoacetal or aminoketal of formula $H_2NCHR^4CR^3(OR^5)_2$ where $R^5$ is lower alkyl. It will be appreciated that when E is Het$(CH_2)_mZ(CH_2)_nNH$ and Het has a substituent including a primary or secondary amino group, such amino groups should be protected during this reaction. When an aminoketone is used, the reaction will in general be carried out under basic conditions, for example with sodium ethoxide in ethanol, and the reaction gives a compound of structure 4 directly. When an aminoacetal or aminoketal is used, the reaction is preferably carried out under neutral conditions, for example in boiling ethanol, and the product cyclised under acidic conditions, for example by treatment with hydrogen chloride in a solvent (for example ether or a lower alkanol), to give a compound of Structure 4. A compound of Structure 4 in which E is QS— can be converted into a compound of Structure 2 wherein X is QSO— by reaction with one equivalent of hydrogen peroxide, and it can be converted into a compound of Structure 2 wherein X is $QSO_2$— by reaction with two equivalents or more of hydrogen peroxide.

The intermediates of Structure 2 where X is $HS(CH_2)_nNH$— can be prepared by reacting a compound of Structure 2 where X is QSO— or $QSO_2$— with an amine of formula $HS(CH_2)_nNH_2$.

The compounds of Structure 1 block histamine $H_2$-receptors; that is, they inhibit the biological actions of histamine which are not inhibited by "antihistamines" such as mepyramine but are inhibited by burimamide. For example, they inhibit histamine-stimulated secretion of gastric acid from the lumen-perfused stomachs of rats anaesthetised with urethane, at doses of from 0.5 to 256 micromoles per kilogram intravenously. Their activity as histamine $H_2$-receptor antagonists is also demonstrated by their ability to inhibit other actions of histamine which are not mediated by histamine $H_1$-receptors. For example, they inhibit the actions of histamine on the isolated guinea pig atrium and isolated rat uterus. They inhibit the basal secretion of gastric acid and also that stimulated by pentagastrin or by food. In a conventional test such as the measurement of blood pressure in the anaesthetised cat, at doses of from 0.5 to 256 micromoles per kilogram intravenously, they inhibit the vasodilator action of histamine. The potency of the compounds is illustrated by an effective dose producing 50% inhibition of gastric acid secretion in the anaesthetised rat and 50% inhibition of histamine-induced tachycardia in the isolated guinea pig atrium (less than $10^{-4}$ Molar).

The pharmaceutical compositions of this invention comprise a pharmaceutical carrier and a compound of Structure 1 in the form of a free base or in the form of a pharmaceutically acceptable acid addition salt. Such addition salts include those with hydrochloric, hydrobromic, hydriodic, sulphuric and maleic acids, and the salts can conveniently be formed from the corresponding bases by standard procedure, for example by reacting the base with an acid in a lower alkanol or by the use of ion exchange resins to form the required salt either directly from the base or from a different addition salt.

The pharmaceutical carrier employed can be solid or liquid. Examples of solid carriers are lactose, terra alba, sucrose, talc, gelatin, agar, pectin, acacia, magnesium stearate and stearic acid. Examples of liquid carriers are syrup, peanut oil, olive oil and water.

If a solid carrier is used, the compositions can be prepared in the form of a tablet, capsule, troche or lozenge. The amount of solid carrier in a unit dosage form will generally be from about 25 mg to about 300 mg. If a liquid carrier is used, the compositions can be in the form of a syrup, emulsion, soft gelatin capsule, a sterile injectable liquid for example contained in an ampoule, or an aqueous or non-aqueous liquid suspension. The pharmaceutical compositions can be prepared by conventional techniques involving procedures such as mixing, granulating and compressing or dissolving the ingredients as appropriate to the desired form of composition. The compositions of the present invention are preferably in dosage unit form each containing an effective amount of active ingredient to block histamine H$_2$-receptors. Each dosage unit preferably contains the active ingredient in an amount of from about 50 mg to about 250 mg.

The invention provides a method of blocking histamine H$_2$-receptors which comprises administering to a subject an effective amount of a compound of Structure 1.

The active ingredient is preferably administered from one to six times per day. The daily dosage regimen will generally be from about 150 mg to about 1500 mg.

The route of administration can be oral or parenteral.

The invention is illustrated by the following Examples wherein temperatures are in degrees Centigrade.

EXAMPLE 1

(a)(i) A solution of aminoacetaldehyde diethylacetal (8 g, 0.06 mol) and 1-nitro-2,2-bis-methylthioethylene (10 g, 0.06 mol) in ethanol (100 ml) was refluxed for 20 hours. The solvent was removed in vacuo. The residue was chromatographed on a silica gel column eluted with carbon tetrachloride/chloroform (7:3) and the product was crystallised from propan-2-ol to give 1-nitro-2-methylthio-2-(2,2-diethoxyethylamino)ethylene (8.7 g, 58%) m.p. 73°–73.5°.

(ii) A solution of aminoacetaldehyde diethylacetal (11 g, 0.08 mol and 1-nitro-2-methylthio-2-methylsulphinylethylene (15 g, 0.08 mol) in methanol (200 ml) was stirred for 2½ hours at room temperature. The solvent was removed in vacuo leaving a yellow oily residue which after trituration with propan-2-ol gave 1-nitro-2-methylthio-2-(2,2-diethoxyethylamino)ethylene (9.8, 49%) m.p. 72°–74°.

(b) Dry hydrogen chloride was passed through a stirred solution of 1-nitro-2-methylthio-2-(2,2-diethoxyethylamino)ethylene (9.7 g, 0.04 mol) in dry ether (250 ml) at 5°–10° for 3 hours. The resulting mixture was basified by pouring it into potassium carbonate solution (300 ml). The mixture was filtered to give a yellow solid, and the aqueous phase of the filtrate was separated and extracted with ether (2×150 ml). The combined ether solutions were evaporated to a residue. This residue and the solid filtered off earlier were recrystallised from acetone-chloroform to give 2-methylthio-3-nitropyrrole (3.4 g, 54%) m.p. 212°–213°.

Found: C, 38.0; H, 3.8; N, 17.7; S, 20.1; C$_5$H$_6$N$_2$O$_2$S. Requires: C, 38.0; H, 3.8; N, 17.7; S, 20.3%.

(c) A solution of 2-methylthio-3-nitropyrrole (2.5 g, 0.016 mol) in glacial acetic acid (70 ml) and hydrogen peroxide (2 ml, 0.017 mol, 100 vol) was heated at 60° for 4½ hours. The solvent was removed in vacuo (after first checking that no peroxide remained), and the residue was recrystallised from propan-2-ol to give 2-methylsulphinyl-3-nitropyrrole (2.3 g, 85% m.p. 162°–164°.

Found: C, 34.45; H, 3.4; N, 15.9; S, 18.3; C$_5$H$_6$N$_2$O$_3$S. Requires: C, 34.5; H, 3.5; N, 16.1; S, 18.4%.

(d) A solution of 2-methylsulphinyl-3-nitropyrrole (2 g, 0.01 mol) and 2-(5-methyl-4-imidazolylmethylthio)ethylamine (2 g, 0.01 mol) in methanol (50 ml) was refluxed for 7 days and evaporated to dryness. The residue was chromatographed on a silica gel column eluted with ethyl acetate, and the eluate was evaporated to dryness and recrystallised from propan-2-ol to give 2-[2-(5-methyl-4-imidazolylmethylthio)ethylamino]-3-nitropyrrole (0.96 g, 31%) m.p. 161°–162°.

Found: C, 46.9; H, 5.45; N, 24.6; S, 11.0; C$_{11}$H$_{15}$N$_5$O$_2$S. Requires: C, 47.0; H, 5.4; N, 24.9; S, 11.4%.

EXAMPLE 2

(a) Crushed potassium hydroxide (5.7 g, 0.1 mol) was added portionwise to a refluxing solution of 1-nitro-2-methylthio-2-methylsulphinylethylene (9.3 g, 0.05 mol) and aminoacetone hydrochloride (5.6 g, 0.05 mol) in methanol (100 ml). Reflux was continued for 5 minutes, and then the mixture was cooled and the solvent removed in vacuo. Water was added to the residue, and the solid was recrystallised from chloroform/methanol/petroleum ether to give 2-methylthio-3-nitro-4-methylpyrrole (1.45 g, 16%) m.p. 216–216-5.

Found: C, 41.9; H, 4.6; N, 16.2; S, 18.8; C$_6$H$_8$N$_2$O$_2$S. Requires: C, 41.85; H, 4.7; N, 16.3; S, 18.6%.

(b) Substitution of an equivalent amount of 2-methylthio-3-nitro-4-methylpyrrole for 2-methylthio-3-nitropyrrole in the procedure of Example 1(c) gave 2-methylsulphinyl-3-nitro-4-methylpyrrole in 82% yield, m.p. 161°–162° (ethyl acetate).

Found: C, 38.5; H, 4.4; N, 14.9; S, 16.9; C$_6$H$_8$N$_2$O$_3$S. Requires: C, 38.3; H, 4.3; N, 14.9; S, 17.0%.

(c) Substitution of an equivalent amount of 2-methylsulphinyl-3-nitro-4-methylpyrrole for 2-methylsulphinyl-3-nitropyrrole in the procedure of Example 1(d) gave 2-[2-(5-methyl-4-imidazolylmethylthio)ethylamino]-3-nitro-4-methylpyrrole, m.p. 172° in 25% yield.

Found: C, 48.95; H, 6.0; N, 23.8; S, 10.8; C$_{12}$H$_{17}$N$_5$O$_2$S. Requires: C, 48.8; H, 5.8; N, 23.7; S, 10.9%.

EXAMPLE 3

(a) A solution of sodium methoxide (sodium (1.9 g, 0.084 mol) dissolved in methanol (100 ml)) and a solution of 1-amino-3-phenylpropan-2-one hydrochloride (7.9 g, 0.042 mol) in methanol (100 ml) were simultaneously added dropwise, to a stirred solution of 1-nitro-2-methylthio-2-methylsulphinylethylene (7.7 g, 0.042 mol) in methanol. The temperature was maintained at about 60° during the addition, which took 25 minutes. The solvent was then removed in vacuo, and the residual dark red oil was chromatographed on a silica gel column. Elution and recrystallisation with petroleum ether/ethyl acetate (7:3) gave 2-methylthio-3-nitro-4-benzylpyrrole (2.95 g, 28.5%) m.p. 190°–192.5°.

Found: C, 57.8; H, 4.85; N, 11.35; S, 12.6; C$_{12}$H$_{12}$N$_2$O$_2$S. Requires: C, 58.05; H, 4.9; N, 11.3; S, 12.9%.

(b) Substitution of an equivalent amount of 2-methylthio-3-nitro-4-benzylpyrrole for 2-methylthio-3-nitropyrrole in the procedure of Example 1(c) gave 2-methylsulphinyl-3-nitro-4-benzylpyrrole (1.7 g, 58%) m.p. 189°–190° (ethyl acetate).

Found: C, 54.3; H, 4.6; N, 10.7; S, 11.9; C$_{12}$H$_{12}$N$_2$O$_3$S. Requires: C, 54.5; H, 4.6; N, 10.6; S, 12.1%.

(c) Substitution of an equivalent amount of 2-methylsulphinyl-3-nitro-4-benzylpyrrole for 2-methylsulphinyl-3-nitropyrrole in the procedure of Example 1(d) gave 2-[2-(5-methyl-4-imidazolylmethylthio)ethylamino]-3-nitro-4-benzylpyrrole (1.08 g, 52%) m.p. 192.5°–193°.

Found: C, 58.6; H, 5.7; N, 18.9; S, 8.5; C$_{18}$H$_{21}$N$_5$O$_2$S. Requires: C, 58.2; H, 5.7; N, 18.85; S, 8.6%.

EXAMPLE 4

(a) α-Aminoacetophenone hydrochloride (6.87 g, 0.040 mol) was mixed with 1-nitro-2-methylthio-2-methylsulphinylethylene (7.25 g, 0.040 mol) in 300 ml dry methanol and warmed at 60°. Sodium methoxide (from 0.92 g sodium, 0.080 g atom) in methanol (25 ml) was added dropwise, with stirring, over about 10 minutes. After addition, the mixture was stirred at 60° for one hour, and then filtered to give 2-methylthio-3-nitro-4-phenylpyrrole 5.66 g, m.p. 259°–261° dec.

Found: C, 56.0; H, 4.3; N, 11.85; C$_{11}$H$_{10}$N$_2$O$_2$S. Requires: C, 56.4; H, 4.3; N, 12.0%.

(b) 2-Methylthio-3-nitro-4-phenylpyrrole (3.00 g, 0.013 mol) was suspended in glacial acetic acid (200 ml), and 30% hydrogen peroxide (1.45 g, 0.013 mol) was added. The mixture was stirred at 80° for five hours, after which the mixture was evaporated to dryness and the solid residue was recrystallised from isopropanol to give 2-methylsulphinyl-3-nitro-4-phenyl pyrrole (2.52 g), m.p. 197° dec.

Found: C, 52.5; H, 4.05; N, 11.3; C$_{11}$H$_{10}$N$_2$O$_3$S. Requires: C, 8; H, 4.0; N, 11.2%.

(c) 2-Methylsulphinyl-3-nitro-4-phenylpyrrole (2.0 g, 0.008 mol) was partially dissolved in ethanol (150 ml) and a solution of 2-(5-methyl-4-imidazolylmethylthio)ethylamine (1.37 g, 0.008 mol) in a little ethanol was added to it. The mixture was refluxed for seven days, after which the mixture was stripped and chromatographed on a silica gel column, collecting the required product by elution with ethyl acetate. The crude solid was recrystallised from 2-propanol to give 2-[2-(5-methyl-4-imidazolylmethylthio)ethyl]amino-3-nitro-4-phenylpyrrole (0.46 g), m.p. 182°–184°.

Found: C, 56.8; H, 5.5; N, 19.8; S, 8.7; C$_{17}$H$_{19}$N$_5$O$_2$S. Requires: C, 57.1; H, 5.4; N, 19.6; S, 9.0%.

EXAMPLE 5

(a) Substitution of an equivalent amount of 1-amino-4-phenylbutan-2-one hydrochloride for 1-amino-3-phenylpropan-2-one hydrochloride in the procedure of Example 3(a) gave 2-methylthio-3-nitro-4-(2-phenylethyl)pyrrole m.p. 198°–200°.

(b) Substitution of an equivalent amount of 2-methylthio-3-nitro-4-(2-phenylethyl)pyrrole for 2-methylthio-3-nitropyrrole in the procedure of Example 1(c) gave 2-methylsulphinyl-3-nitro-4-(2-phenylethyl)pyrrole m.p. 171.5°–173° in 75% yield.

(c) Substitution of an equivalent amount of 2-methylsulphinyl-3-nitro-4-(2-phenylethyl)pyrrole for 2-methylsulphinyl-3-nitropyrrole in the procedure of Example 1(d) gave 2-[2-(5-methyl-4-imidazolylmethylthio)ethylamino]-3-nitro-4-(2-phenylethyl)pyrrole m.p. 186°–187° in 31% yield.

EXAMPLE 6

(i) Sodium hydride (50% in oil, 39.6 g) was added portionwise to a solution of ethyl acetoacetate (107.5 g) in dry ether under nitrogen. Valeryl chloride (100 g) was added dropwise over 2½ hours to the stirred suspension, and then poured into distilled water (500 ml.), and the ether layer was separated off and dried. The ether was removed to give ethyl 2-valerylacetoacetate (142 g) as a yellow oil.

(ii) A solution of sodium nitrite (41.3 g) in water was added slowly to a cooled solution of ethyl 2-valerylacetoacetate (118.7 g) in acetic acid (100 ml.), and the temperature was kept below 10°. Ice (100 g) was added, followed by acetic anhydride (105.0 g). Zinc dust (total 65.4 g) was added portionwise, keeping the temperature below 20° with stirring, until the reaction was complete. The mixture was allowed to stand overnight at room temperature, and it was then filtered. The solid was washed with chloroform, and the filtrate was extracted with chloroform. The chloroform extracts were washed with sodium carbonate solution and dried. The solvent was removed under vacuum, and the residue was purified by column chromatography (silica gel) eluting with petroleum ether (b.p. 60°–80°)/ethyl acetate, to yield ethyl-2-acetamido-3-oxoheptanoate, 13.5 g, which was used without further purification.

(iii) Ethyl 2-acetamido-3-oxoheptanoate (10.4 g) was hydrolysed by heating under reflux with 50% hydrochloric acid (80 ml) for 9 hours. The mixture was evaporated to dryness to give 1-amino-2-hexanone hydrochloride (5.8 g) as a dark red oil.

(iv) 1-Amino-2-hexanone hydrochloride (5.8 g) was dissolved in methanol (100 ml) and mixed with a solution of 1-methylthio-1-methylsulphinyl-2-nitroethylene (6.8 g) in warm methanol (100 ml). A solution of sodium methoxide in methanol (from 1.7 g sodium) was added dropwise, with stirring, over 2 hours at 60°, and the mixture was evaporated to dryness. The residue was triturated with water, and the solid was filtered off and dried, to give 2-methylthio-3-nitro-4-n-butylpyrrole (3.9 g).

(v) 2-Methylthio-3-nitro-4-n-butylpyrrole (3.7 g) was suspended in glacial acetic acid (50 ml) and 30% hydrogen peroxide (1.62 g) was added. The mixture was heated to 80° for 7 hours, and it was then evaporated to a brown oil. The crude product was purified by column chromatography using silica gel, eluted with benzene and chloroform, to give an oil which crystallized on standing. This was recrystallised from 2-propanol to give 2-methylsulphinyl-3-nitro-4-n-butylpyrrole (1.6 g), m.p. 133°–4°.

(vi) 2-Methylsulphinyl-3-nitro-4-n-butylpyrrole (2.78 g) was dissolved in ethanol and added to a solution of 2-(5-methyl-4-imidazolylmethylthio)ethylamine (2.08 g) in ethanol (total 100 ml). The mixture was heated under reflux for nine days. The solution was evaporated to dryness, and the residue was chromatographed on a silica gel column using chloroform and ethyl acetate to give 0.65 g of crude product as a brown oil. The crude product was dissolved in isopropanol (30 ml) and reacted with a solution of maleic acid (0.5 g) in 2-propanol. The mixture was warmed on a steam bath for a few minutes and then allowed to cool, yielding bright yellow crystals of 2-[2-(5-methyl-4-imidazolylmethylthio)ethyl]amino-3-nitro-4-n-butylpyrrole maleate (0.19 g), m.p. 94°–95°.

EXAMPLE 7

2-(3-Chloro-2-pyridylmethylthio)ethylamine dihydrobromide (1.22 g) was neutralized by reaction with aqueous sodium hydroxide, and the free base was extracted into chloroform. After evaporation of solvent, the base was dissolved in ethanol and added to an ethanolic solution of 2-methyl-sulphinyl-3-nitropyrrole (0.59 g). The mixture was refluxed for ten days, evaporated to dryness, and the residue was chromatographed on a column of silica gel eluted with chloroform. The crude product was recrystallised from 2-propanol to give 2-[2-(3-chloro-2-pyridylmethylthio)ethylamino]-3-nitropyrrole, m.p. 144°-147° dec.

Found: C, 45.98; H, 4.20; N, 17.57; $C_{12}H_{13}N_4O_2SCl$. Requires: C, 46.08; H, 4.19; N, 17.91%.

EXAMPLE 8

A solution of 2-(5-dimethylaminomethyl-2-furylmethylthio)ethylamine (3 g, 0.014 mol) and 2-methylsulphinyl-3-nitropyrrole (2 g, 0.011 mol) in ethanol (50 ml) was refluxed for 7 days, and it was then evaporated to dryness. The residue was purified by elution from a column of silica gel with ethyl acetate-petroleum ether (b.p. 60°-80°)(4:1) to give 2-[2-(5-dimethylaminomethyl-2-furylmethylthio)ethylamino]-3-nitropyrrole, m.p. 67°-67°.

EXAMPLES 9 to 31

Substitution of an equivalent amount of:
(a) 2-(2-imidazolylmethylthio)ethylamine
(b) 2-(4-imidazolylmethylthio)ethylamine
(c) 2-(5-bromo-4-imidazolylmethylthio)ethylamine
(d) 2-(5-trifluoromethyl-4-imidazolylmethylthio)ethylamine
(e) 2-(5-hydroxymethyl-4-imidazolylmethylthio)ethylamine
(f) 2-(2-pyridylmethylthio)ethylamine
(g) 2-(3-methyl-2-pyridylmethylthio)ethylamine
(h) 2-(3-methoxy-2-pyridylmethylthio)ethylamine
(i) 2-(3-amino-2-pyridylmethylthio)ethylamine
(j) 2-(3-hydroxy-2-pyridylmethylthio)ethylamine
(k) 2-(3-isothiazolylmethylthio)ethylamine
(l) 2-(4-bromo-3-isothiazolylmethylthio)ethylamine
(m) 2-(3-(1,2,5)-thiadiazolylmethylthio)ethylamine
(n) 2-(4-chloro-3-(1,2,5)-thiadiazolylmethylthio)ethylamine
(o) 2-(5-amino-2-(1,3,4)-thiadiazolylmethylthio)ethylamine
(p) 2-((5-dimethylaminomethyl)-2-furyl)methylthio)ethylamine
(q) 2-((5-methylaminomethyl)-2-furyl)methylthio)ethylamine
(r) 2-((5-(1-pyrrolidino)methyl)-2-furyl)methylthio)ethylamine
(s) 2-((5-methylethylaminomethyl-2-furyl)methylthio)ethylamine
(t) 2-((5-dimethylaminomethyl)-2-thienyl)methylthio)ethylamine
(u) 2-((5-methylaminomethyl)-2-thienyl)methylthio)ethylamine
(v) 2-((5-(1-pyrrolodino)methyl)-2-thienyl)methylthio)ethylamine
(w) 2-((5-methylethylaminomethyl-2-thienyl)methylthio)ethylamine for 2-(5-methyl-4-imidazolylmethylthio)ethylamine in the procedure of Example 1 leads to the production of:

Example Number 9. 2-/2-(2-imidazolylmethylthio)ethylamino/-3-nitropyrrole
10. 2-[2-(4-imidazolylmethylthio)ethylamino]-3-nitropyrrole
11. 2-[2-(5-bromo-4-imidazolylmethylthio)ethylamino]-3-nitropyrrole
12. 2-[2-(5-trifluoromethyl-4-imidazolylmethylthio)ethylamino]-3-nitropyrrole
13. 2-[2-(5-hydroxymethyl-4-imidazolylmethylthio)ethylamino]-3-nitropyrrole
14. 2-[2-(2-pyridylmethylthio)ethylamino]-3-nitropyrrole
15. 2-[2-(3-methyl-2-pyridylmethylthio)ethylamino]-3-nitropyrrole
16. 2-[2-(3-methoxy-2-pyridylmethylthio)ethylamino]-3-nitropyrrole
17. 2-[2-(3-amino-2-pyridylmethylthio)ethylamino]-3-nitropyrrole
18. 2-[2-(3-hydroxy-2-pyridylmethylthio)ethylamino]-3-nitropyrrole
19. 2-[2-(3-isothiazolylmethylthio)ethylamino]-3-nitropyrrole
20. 2-[2-(4-bromo-3-isothiazolylmethylthio)ethylamino]-3-nitropyrrole
21. 2-[2-(3-(1,2,5)-thiadiazolylmethylthio)ethylamino]-3-nitropyrrole
22. 2-[2-(4-chloro-3-(1,2,5)-thiadiazolylmethylthio)ethylamino]-3-nitropyrrole
23. 2-[2-(5-amino-2-(1,3,4)-thiadiazolylmethylthio)ethylamino]-3-nitropyrrole
24. 2-[2-(5-dimethylaminomethyl)-2-furylmethylthio)ethylamino]-3-nitropyrrole
25. 2-[2-(5-(methylaminomethyl)-2-furylmethylthio)ethylamino]-3-nitropyrrole
26. 2-[2-(5-(1-pyrrolidinomethyl)-2-furylmethylthio)ethylamino]-3-nitropyrrole
27. 2-[2-(5-(methylethylaminomethyl)-2-furylmethyl)thio)ethylamino]-3-nitropyrrole
28. 2-[2-(5-(dimethylaminomethyl)-2-thienylmethylthio)ethylamino]-3-nitropyrrole
29. 2-[2-(5-(methylaminomethyl)-2-thienylmethylthio)ethylamino]-3-nitropyrrole
30. 2-[2-(5-(1-pyrrolidinomethyl)-2-thienylmethylthio)ethylamino]-3-nitropyrrole
31. 2-[2-(5-(methylethylaminomethyl)-2-thienylmethyl)thio)ethylamino]-2-nitropyrrole

EXAMPLES 32 TO 35

Substitution of an equivalent amount of:
(a) 4-(3-thiazolyl)butylamine
(b) 4-(3-oxazolyl)butylamine
(c) 4-(2-isoxazolyl)butylamine
(d) 4-[3-(1,2,4-triazolyl)]butylamine for 2-(5-methyl-4-imidazolylmethylthio)ethylamine in the procedure of Example 1 leads to the production of:

Example Number 32. 2-[4-(3-thiazolyl)butylamino]-3-nitropyrrole
33. 2-[4-(3-oxazolyl)butylamino]-3-nitropyrrole
34. 2-[4-(2-isoxazolyl)butylamino]-3-nitropyrrole
35. 2-[4-(3-(1,2,4-triazolyl))butylamino]-3-nitropyrrole

EXAMPLE 36

A pharmaceutical composition is prepared from the following ingredients:

2-[2-(5-methyl-4-imidazolylmethylthio)ethylamino]-3-nitropyrrole: 150 mg
Sucrose: 75 mg
Starch: 25 mg
Talc: 5 mg
Stearic Acid: 2 mg The ingredients are screened, mixed and filled into a hard gelatin capsule.

The other compounds of Structure 1 can be formulated into pharmaceutical compositions in a similar manner, and these compositions are administered to a

We claim:
1. A compound represented by Structure 1:

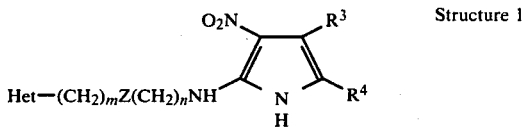

Structure 1 in which
Het is selected from the group consisting of oxazole, isoxazole and 1,2,4-triazole rings optionally substituted by lower alkyl, trifluoromethyl, hydroxymethyl, halogen, hydroxy, lower alkoxy or amino;
Z is sulphur, methylene or oxygen;
m is 0, 1 or 2 and n is 2 or 3 provided that m+n is 3 or 4;
$R^3$ is hydrogen, lower alkyl, aryl, aryl lower alkyl or heteroaryl lower alkyl, aryl being phenyl optionally substituted by lower alkyl, lower alkoxy or halogen and heteroaryl being 2-furyl, 2-thienyl, 2-pyridyl, 3-pyridyl or 4-pyridyl optionally substituted by lower alkyl or lower alkoxy; and
$R^4$ is hydrogen or lower alkyl, or a pharmaceutically acceptable acid addition salt thereof.

2. A compound according to claim 1, where —(CH$_2$)$_m$— is linked to a carbon atom of the heterocycle Het adjacent to a nitrogen atom.

3. A compound according to claim 1, where $R^4$ is methyl.

4. A method of blocking histamine H$_2$-receptors which comprises administering an effective amount of a compound of claim 1 to an animal in need of such treatment.

5. A pharmaceutical composition to block histamine H$_2$-receptors comprising, in an effective amount to block said receptors, a compound according to claim 1 and a pharmaceutical carrier.

* * * * *